United States Patent [19]

Trauthen et al.

[11] Patent Number: 5,263,928
[45] Date of Patent: Nov. 23, 1993

[54] CATHETER AND ENDOSCOPE ASSEMBLY AND METHOD OF USE

[75] Inventors: Brett Trauthen, Corona del Mar; Manouchehr Miraki, Corona, both of Calif.

[73] Assignee: Baxtet International Inc., Deerfield, Ill.

[21] Appl. No.: 715,529

[22] Filed: Jun. 14, 1991

[51] Int. Cl.$^5$ .............................................. A61M 31/00
[52] U.S. Cl. ........................................ 604/53; 604/96; 604/280; 128/4; 128/772
[58] Field of Search .................... 604/96, 100–103, 604/280, 49, 53; 606/14–16, 192, 194; 128/656–658, 772, 4

[56] References Cited

U.S. PATENT DOCUMENTS

| | | | |
|---|---|---|---|
| 4,662,368 | 5/1987 | Hussein et al. | |
| 4,738,659 | 4/1988 | Sleiman | 604/96 |
| 4,771,777 | 9/1988 | Horzewski et al. | 604/101 X |
| 4,773,413 | 9/1988 | Hussein et al. | |
| 4,793,326 | 12/1988 | Shishido | 128/4 |
| 4,824,435 | 4/1989 | Giesy et al. | 604/49 |
| 4,830,460 | 5/1989 | Goldenberg | |
| 4,844,062 | 7/1989 | Wells | |
| 4,928,693 | 5/1990 | Goodin et al. | 128/637 |
| 4,947,864 | 8/1990 | Shockey et al. | 128/772 |
| 4,961,738 | 10/1990 | Mackin | |
| 5,025,778 | 6/1991 | Silverstein et al. | 128/4 |
| 5,127,393 | 7/1992 | McFarlin et al. | 128/4 |

FOREIGN PATENT DOCUMENTS

| | | |
|---|---|---|
| 0112527 | 7/1984 | European Pat. Off. |
| 0119614 | 9/1984 | European Pat. Off. |
| 0177124 | 4/1986 | European Pat. Off. |
| 0338149 | 10/1989 | European Pat. Off. |
| 0370115 | 5/1990 | European Pat. Off. |
| 1918412 | 4/1969 | Fed. Rep. of Germany |
| 2531801 | 7/1975 | Fed. Rep. of Germany |
| 3012150 | 3/1980 | Fed. Rep. of Germany |
| 3425427 | 7/1984 | Fed. Rep. of Germany |
| WO8900023 | 6/1988 | PCT Int'l Appl. |
| WO8901755 | 8/1988 | PCT Int'l Appl. |
| WO8912479 | 6/1989 | PCT Int'l Appl. |
| 2017506 | 10/1979 | United Kingdom |
| 8901755 | 3/1989 | World Int. Prop. O. |

OTHER PUBLICATIONS

Kyoichi Mizuno, M.D. et al, New Percutaneous Transluminal Coronary Angioscope, JACC vol. 123, No. 2, Feb. 1989:363-8.

Arnold Miller, M.B., ChB; et al, "Routine Intraoperative Angioscopy in Lower Extremity Revascularization" Arch Surg-vol. 124, May 1989, 604–608.

Abraham Katzir, "Optical Fibers In Medicine" Scientific American May 1989; 120–125.

Primary Examiner—Michael H. Thaler
Assistant Examiner—C. Maglione
Attorney, Agent, or Firm—Poms, Smith, Lande & Rose

[57] ABSTRACT

A catheter combination as disclosed for passing an endoscope along a vessel. The catheter combination includes a catheter having a hollow tubular member defining a lumen having a first cross-sectional area. The catheter has a proximal end, a distal end and an irrigation connector at the proximal end of the catheter with a wall defining a passageway connecting with the lumen. An endoscope has an endoscope body with a distal end portion and a proximal end portion. The body has a cross-sectional area less than the first cross-sectional area of the lumen. The endoscope proximal end portion extends proximally of the catheter proximal end and the endoscope distal end portion extends distally of the catheter distal end. The endoscope body extends through the lumen such that fluid from the passage in the irrigation connector can pass between the endoscope body and the lumen.

15 Claims, 4 Drawing Sheets

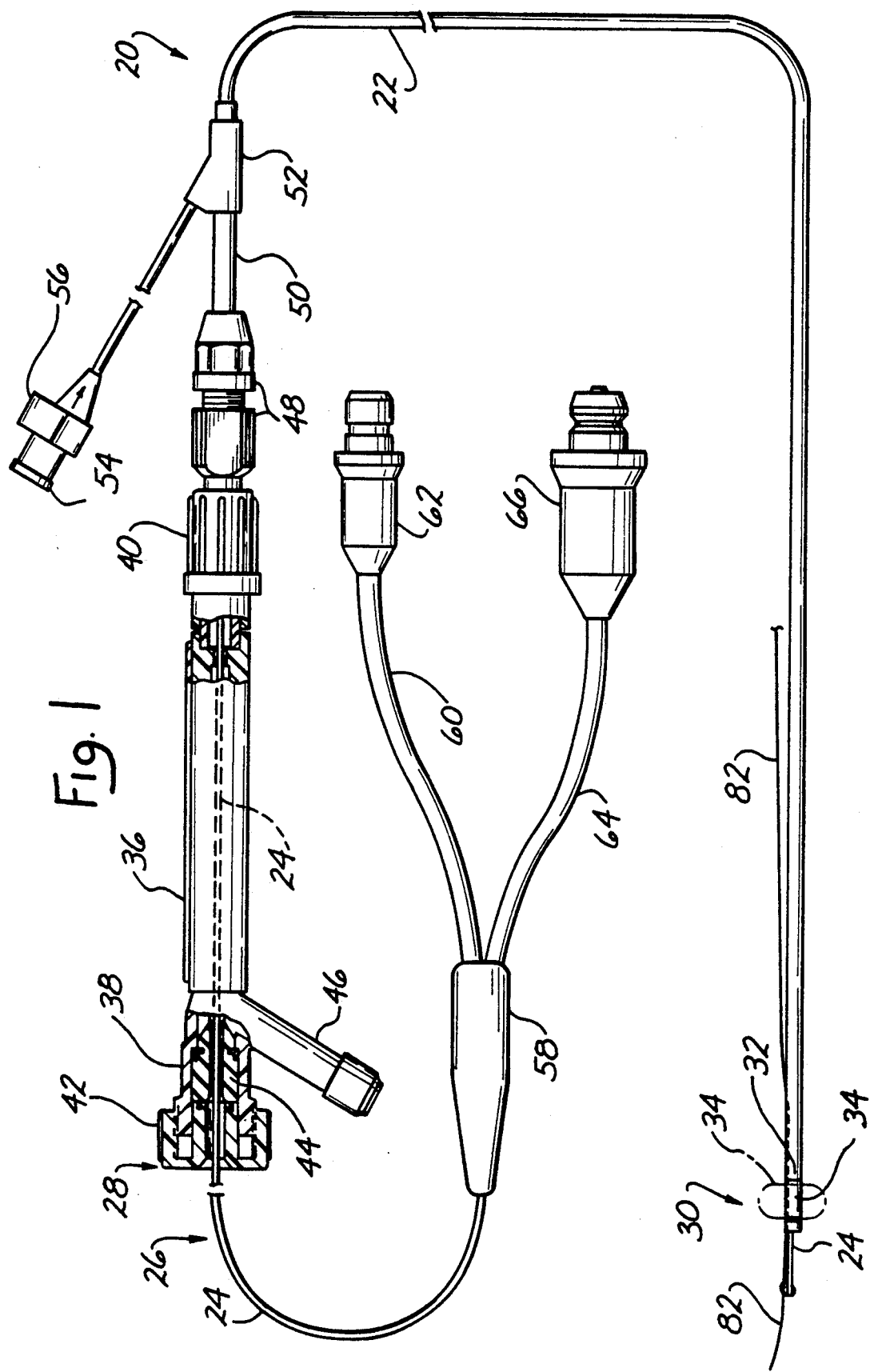

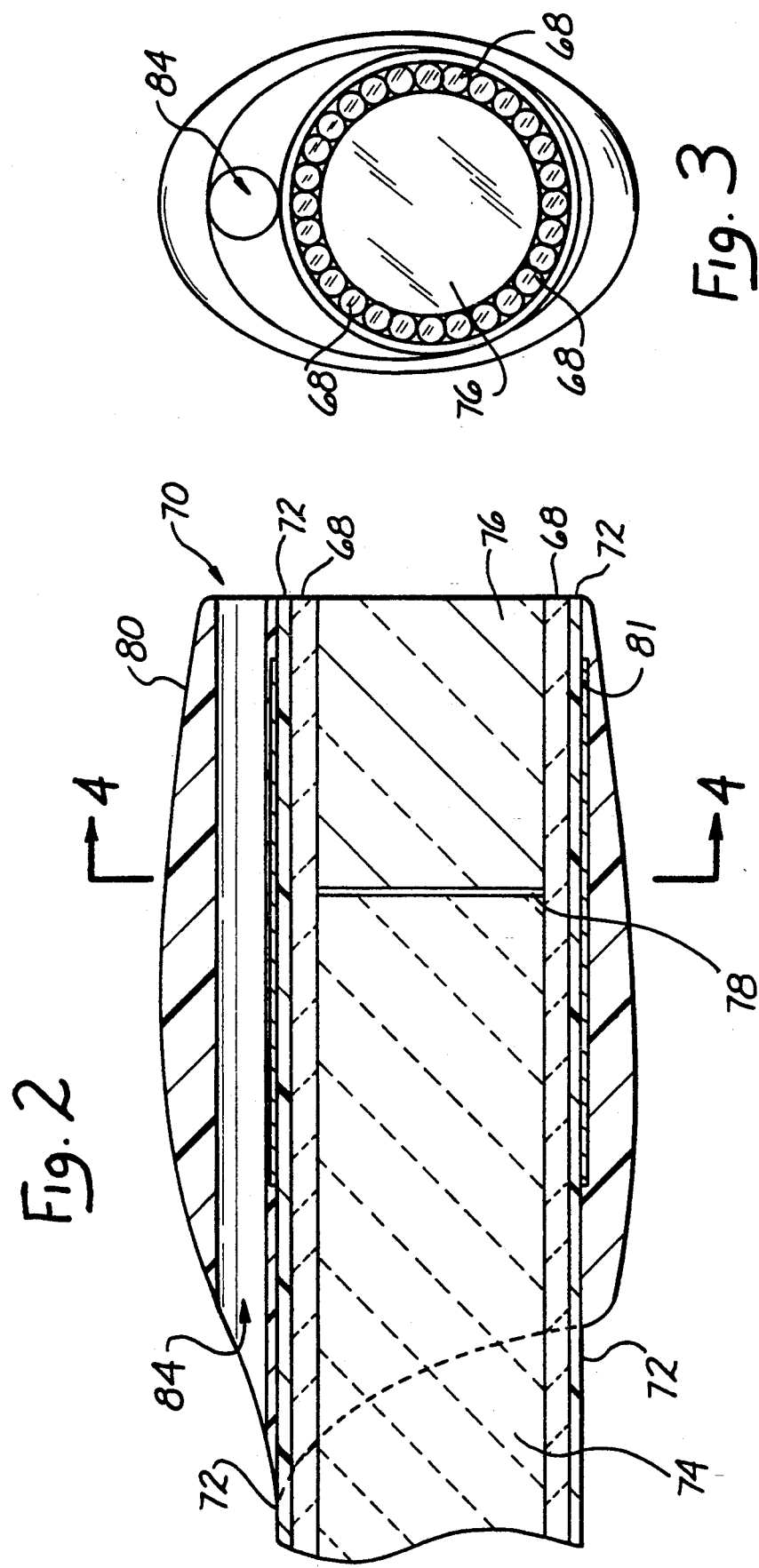

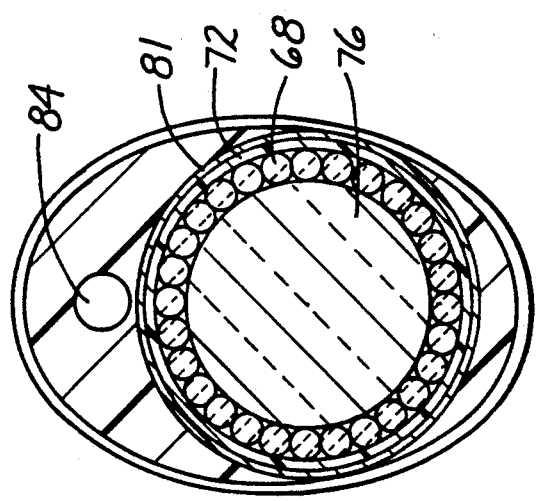
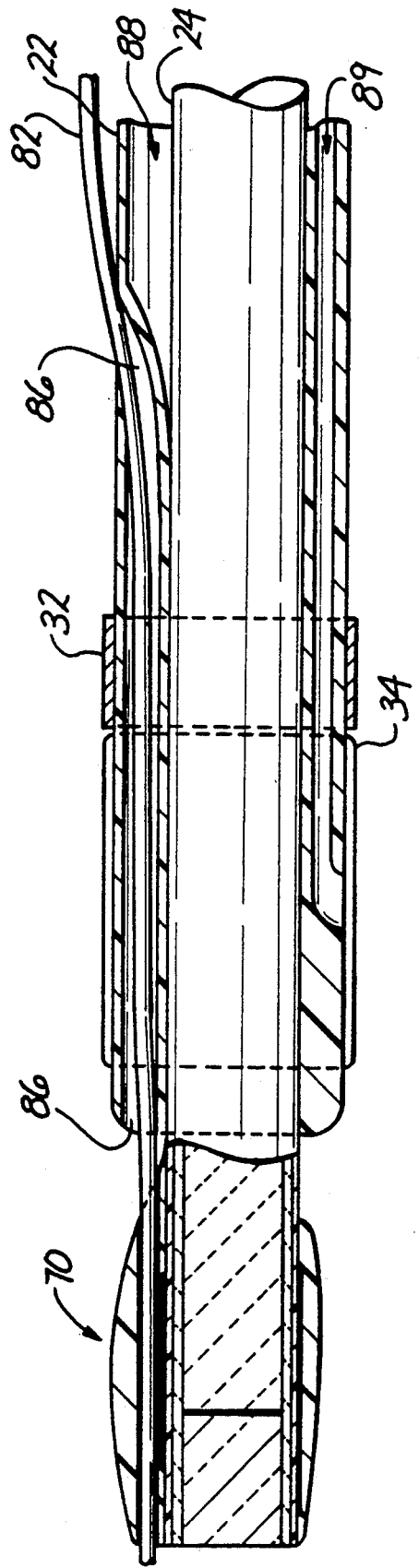

CATHETER AND ENDOSCOPE ASSEMBLY AND METHOD OF USE

BACKGROUND OF THE INVENTION

1. Field of the Invention

The present invention relates to the field of catheters employed in the observation, diagnosis and treatment of vessels, body cavities and the like. More particularly, the present invention relates to a catheter combination that can position a medical instrument such as an endoscope quickly and easily inside body cavities and vessels, and especially small vessels such as cardiac arteries, and locate, evaluate and treat conditions in such areas.

2. Related Art

Catheter assemblies have been used, for example, to view and clear obstructions from various vessels such as cardiac arteries and the like. Such vessels may have become occluded by deposits and need to be explored for possible treatment, such as by angioplasty. The occlusion must first be located, preferably as quickly and easily as possible to minimize any possible trauma or complications as a result of the procedure. Once located, the operator can apply lasers, angioplasty or other methods to treat the occluded vessel.

In the past, treating physicians may have used multiple lumen catheters that accepted medical instruments, such as lasers, angioscopes and guide wires to get inside a vessel or artery to remove the occlusion. Hussein et al., U.S. Pat. No. 4,773,413, shows such a device. One of the problems with multiple lumen catheters is that they are relatively bulky and stiff, which sometimes causes vessel damage. Another problem is that these bulky, stiff catheters sometimes have difficultly passing through the tortuous passages of the vessels.

A steerable guide wire may be used to guide a catheter along a vessel to an obstruction within the vessel. Such an arrangement is shown in Wells, U.S. Pat. No. 4,844,062. The catheter includes two lumens, wherein an optical fiber is housed in one lumen of the catheter and the guide wire is housed in a second lumen of the catheter parallel to the first lumen to reduce perforations to the vessel wall.

Multi-lumen catheters and internally disposed guide wires result in bulky and often stiff catheter tubes which are difficult to manipulate and which are often able to access only relatively larger vessels. There is a need for a catheter and endoscope combination which allows the endoscope to access and traverse relatively small diameter body cavities and vessels. There is also a need for a catheter endoscope combination wherein the endoscope is moveable independently of the catheter while still maintaining the catheter position stable. There is also a need for a catheter endoscope combination wherein the endoscope is moveable relative to the catheter and allows infusion of solutions through the catheter even while the endoscope is in place. Additionally, there is a need for a catheter endoscope combination which uses a guide wire to locate the vessel under consideration and guide the endoscope to the desired location in the vessel, while still allowing the endoscope to be removed and substituted with another instrument.

Accordingly, it is an object of the present invention to provide a catheter and endoscope combination wherein the endoscope is axially moveable relative to the catheter while still maintaining the proper position of the catheter.

It is another object of the present invention to provide a catheter combination having a guide wire which allows removal of the catheter, and re-engagement or replacement of instruments while leaving the guide wire in place to preserve an easily negotiated path along the vessel.

It is an additional object of the present invention to provide a catheter combination offering an extremely low profile and small shaft size to facilitate maneuverability and placement of the catheter, even in tortuous passageways of the vessels.

It is a further object of the present invention to provide a catheter combination with a guide wire that does not need an internal guide wire lumen through the entire length of the catheter. The guide wire in a preferred form of the invention passes external to the main portion of the catheter, eliminating any need for a separate full length guide wire lumen.

It is another object of the present invention to provide an instrument with a guide wire tip having an aperture which will extend past the catheter tip and accept the guide wire at the aperture. The guide wire tip also has a unique outer configuration to minimize any possible trauma to a vessel during its travel in the vessel.

It is yet a further object of the present invention to provide a catheter endoscope combination which allows infusion of solutions through the catheter lumen and around the endoscope bundle.

It is yet another object of the present invention to provide an occlusion cuff catheter combination having one or more of the above-described features. It is a specific object of one form of the present invention to provide an occlusion cuff catheter combination wherein a guide wire extends external to almost the entire length of the catheter but passing internal to a portion of the occlusion cuff. It is a further object to provide an occlusion cuff catheter capable of achieving an effective seal in a vessel and retaining the capability of wire guided access.

It is yet another object of the present invention to provide an improved procedure utilizing a highly maneuverable, low profile, occlusion cuff catheter that uses a guide wire external to the main portion of the catheter along with a instrument that extends past the catheter lumen.

SUMMARY OF THE INVENTION

These and other objects are achieved according to the present invention with a catheter combination including a catheter and an endoscope passing through a lumen of the catheter. The catheter combination allows full use of the endoscope, while keeping the catheter stable, even in very small vessels inaccessible to previous instruments.

More specifically, a catheter combination for passing an endoscope along a vessel includes a catheter with a wall defining a lumen having a first cross-sectional area and wherein the catheter has a proximal end, a distal end and an irrigation connector at the proximal end of the catheter with a wall defining a passageway connecting with the lumen. The endoscope has an endoscope body with a distal end portion and a proximal end portion. The body has a cross-sectional area less than the first cross-sectional area of the lumen. The endoscope proximal end portion extends proximally of the catheter proximal end and the endoscope distal end portion extends distally of the catheter distal end. The endoscope body extends along the lumen in a manner such that fluid from the passage in the irrigation connector can pass between the endoscope body and the lumen. This combination provides a very thin catheter combination so that the combination and ultimately the endoscope can be passed into very small vessels. After the catheter has been properly positioned, the endoscope can still be manipulated to position the tip of the endoscope closer to the object of interest by passing the endoscope further along the vessel, and also to ensure that the object of interest is in proper focus.

In one preferred embodiment of the invention, the catheter is an occlusion cuff catheter with an angioscope already inserted into the primary lumen of the catheter, the secondary lumen of the catheter being for inflating the occlusion cuff. The occlusion cuff ensures proper positioning and stability of the catheter and limits the passage of fluid, such as blood in the vessel, around the tip of the angioscope. Fluid can then be infused through the primary lumen around the angioscope body to clear the area around the angioscope tip for proper viewing.

In another form of the invention, the catheter combination includes a guide wire formed for example of metal, polymeric material, or a combination of both and having a relatively small cross-sectional area. The guide wire extends in the vessel external to at least almost the entire length of the catheter, thereby allowing for a reduced cross-sectional profile for the catheter combination. Where the catheter is an occlusion cuff catheter, the guide wire passes internal to the cuff, preferably by passing through a guide wire lumen external to the catheter lumen, through which the endoscope passes, but internal to the occlusion cuff. The guide wire lumen allows complete inflation of the occlusion cuff and proper occlusion of the subject vessel while still accepting the guide wire. Where the catheter application does not require an occlusion cuff or similar structure, the guide wire may be external to the entire length of the catheter. The guide wire is positioned in the vessel, after which the catheter is threaded with and passed along the same path as the guide wire. With the guide wire in place, the catheter combination can be easily withdrawn and another instrument such as an angioplasty balloon can be passed up the same vessel path after the guide wire is threaded onto an appropriate guide element on the new instrument, thereby eliminating the need for any maneuvering of the instrument to properly position the end of the instrument in ,the vessel of interest. This procedure also minimizes the time required to properly position the new instrument.

The catheter combination has an exceptionally small insertion profile while still allowing substantially unrestricted movement of the angioscope after proper positioning of the catheter. The present invention also allows full use of a guide wire but provides the ability to leave the guide wire in position, for example across a vascular lesion, during instrument exchange or removal.

Other features and advantages of the present invention will become apparent from the following detailed description, taken in conjunction with the accompanying drawings which illustrate, by way of example, the principals of the present invention.

BRIEF DESCRIPTION OF THE DRAWINGS

FIG. 1 is a partial sectional and plan view of a catheter assembly in accordance with one form of the present invention.

FIG. 2 is a longitudinal side sectional view of a portion of an angioscope and a guide rail tip forming part of the catheter assembly in one embodiment of the present invention.

FIG. 3 is a distal end view of the angioscope and the guide rail tip of FIG. 2 showing the shape of the guide rail tip.

FIG. 4 is a transverse sectional view of the angioscope and the guide rail tip of FIG. 2.

FIG. 5 is a longitudinal side sectional view of a portion of the catheter assembly according to one embodiment of the present invention showing a guide wire passing through a guide wire lumen in the catheter tip.

DETAILED DESCRIPTION OF THE PREFERRED EMBODIMENTS

Figure 6:
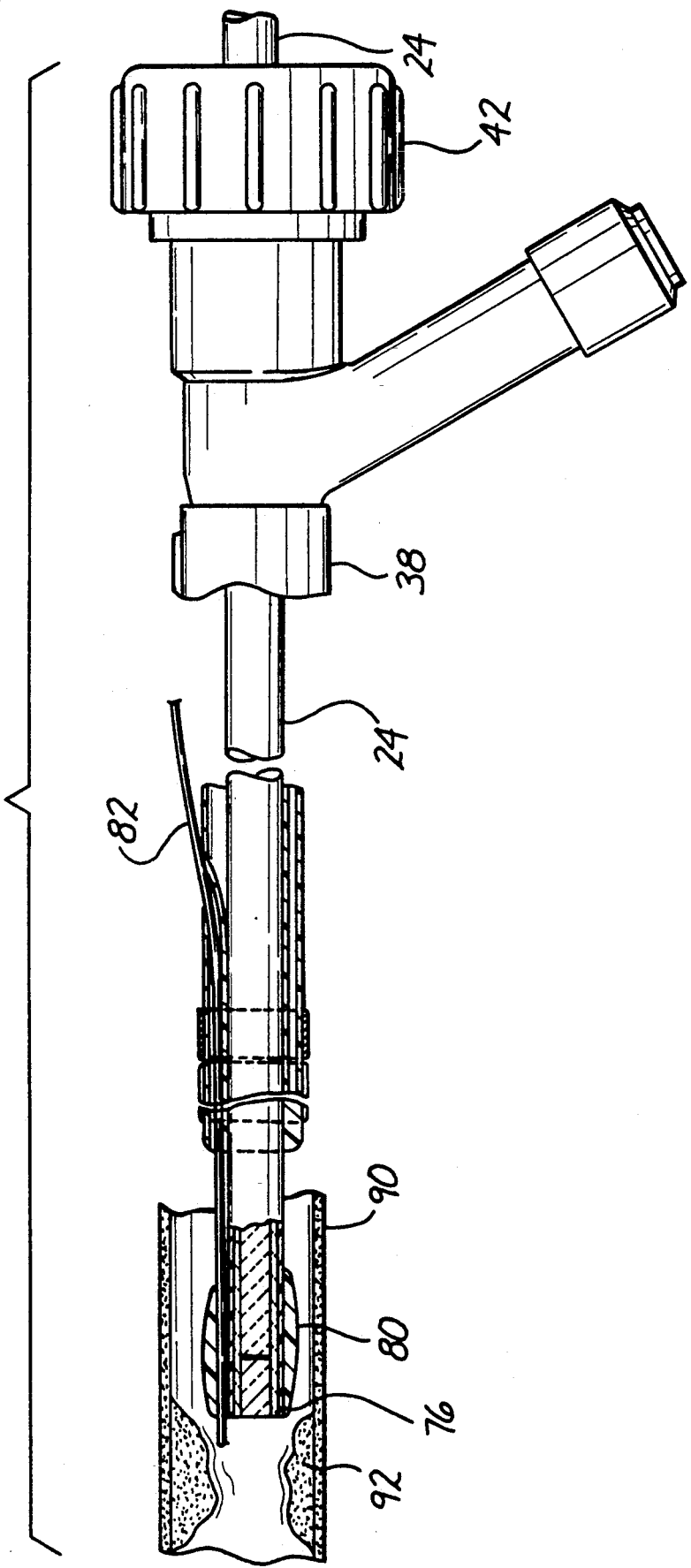
FIG. 6 is a fragmentary and partial side section view of the catheter assembly in a vessel.

In accordance with the invention, the improved catheter assembly 20 (FIG. 1) allows movement of the endoscope independent of the catheter. Where the endoscope is an angioscope, the guide rail tip in combination with a guide wire allows superior access to distal coronary vessels over previously known angioscopes. The construction of the catheter assembly and the guide rail tip for use with the guide wire make the present catheter combination more advantageous than previous catheter assemblies.

The catheter 20 includes a hollow tubular member 22 defining a lumen having a first cross-sectional area through which the bundle 24 of an endoscope 26 will pass. The catheter has a proximal end 28 and a distal end 30, the distal end being introduced into an appropriate vessel or body cavity, such as, in the case of angiography, a brachial or ilial artery. The distal end preferably includes a radiopaque marker 32 and an occlusion cuff 34, as is known to those skilled in the art.

The proximal end 28 of the catheter may include a transparent gauge 36 for measuring the distance from the proximal end of the catheter to the tip of the angioscope bundle 24. The transparent gauge 36 is coupled between a Y-connector 38 and a rotating adaptor 40, the Y-connector 38 and the rotating adaptor 40 being elements well known to those skilled in the art. A Y-connector cap 42 closes off the proximal end of the Y-connector and compresses a sealing element 44 in the barrel of the Y-connector. The bundle 24 of the angioscope passes through an opening in the Y-connector cap 42 and an axially extending channel through the sealing element 44, and through the transparent gauge 36. The Y-connector includes an irrigation duct 46 for injecting fluid through the passage containing the bundle 24 and ultimately into the primary lumen of the catheter, through which the endoscope bundle 24 passes.

A catheter hub is coupled to the distal end of the rotating adapter 40 for coupling the hollow tubular member 22 to the rotating adaptor 40 so that the primary lumen of the hollow tubular member is confluent with the passage through which the bundle 24 passes, and so that any fluid injected into the irrigation duct passes along the primary lumen around the bundle 24. The hollow tubular member is coupled to the catheter hub through a barrel 50 and coupling 52 as is known in the art. The coupling 52 connects a cuff inflation connector 54 and a gate valve 56 to a secondary lumen in the hollow tubular member for inflating the occlusion cuff 34 at the distal end of the catheter. The secondary lumen is sufficiently large to permit adequate inflation of the cuff 34 while minimizing the space taken up by the secondary lumen.

In the preferred embodiment, the endoscope is an angioscope having an optic junction 58 for connecting a light bundle 60 to an appropriate portion of the bundle 24 from a light connector 62 well known to those skilled in the art. The optic junction also connects an optic bundle 64 to an image connector 66, also well known to those skilled in the art.

The light bundle 60 is optically connected to a series of cylindrically arranged optic fibers 68 (FIGS. 2 and 3) running the entire length of the bundle 24 to the distal tip 70 of the bundle. The optic fibers 68 are encased in a sheath 72 to protect the integrity of the optic fibers 68 and the rest of the bundle 24. The optic fibers are exposed at the tip 70 to transmit light from the light connector 62 beyond the distal tip of the angioscope to illuminate an object of interest.

The optic fibers enclose a preferably silica image fiber bundle 74 for transmitting light received by an optic lens 76 and focused on the end of the bundle back to the image connector 66 for transmission to an appropriate focusing coupler, remote head, camera processor, video tape recorder and monitor, as necessary. The optic lens 76 is a glass gradient index lens bonded to the distal end of the optic fiber bundle by an acrylic ester ultraviolet cured adhesive 78.

The distal tip 70 of the bundle 24 includes a guide wire tip 80 for threading a guide wire 82 (FIG. 1) so that the guide wire can guide the bundle and catheter along the desired vessel for proper positioning of the catheter and bundle tip. The guide wire tip 80 (FIGS. 2-4) is a pre-formed plastic tip, preferably formed from polyvinyl chloride (PVC). The tip has a configuration and shape formed specifically to minimize any possible trauma to the vessel being traversed which may result from movement and contact of the tip against the vessel wall. The tip is placed on the distal end of the bundle 24 and secured thereto by an acrylic ester ultraviolet cured adhesive and over a radiopaque marker 81 encircling the distal end of the bundle. An orifice 84 is formed in the tip extending longitudinally thereof so that the orifice 84 extends in a direction parallel to the optic fiber bundle 74.

The outer configuration of the guide wire tip is generally elliptical at approximately the longitudinal midsection. The elliptical portion has a major axis passing through the center of the lens 76 and the center of the orifice 84. The minor axis extends through the lens or bundle, depending on where the section is taken. Both the top and bottom surfaces of the guide wire tip slope outward (i.e., the length of the major axis increases) moving proximally from the distal tip of the guide wire tip. The maximum length of the major axis of the guide wire tip occurs at the approximate longitudinal mid-portion of the tip. From that point proximally, the outer surface of the guide wire tip slopes inwardly toward the surface of the bundle 72. The slope of the back end of the tip as it crosses the orifice at the centerline is approximately 60° from the vertical. Additionally, the rear of the guide wire tip slopes upwardly and backwardly from the bottom of the tip to the top rear edge of the guide wire tip, as shown by the curved, dashed line in FIG. 2. Finally, the width, or length of the minor axis, increases from the distal tip of the guide wire tip to the approximate mid-portion of the tip, after which the width or length of the minor axis decreases to the rear portion of the guide wire tip. This shape of the guide wire tip minimizes the possibility of trauma to the vessel being traversed an nonetheless permits easy passage of the bundle through a vessel.

In a preferred form of the invention, such as where the catheter is an occlusion cuff catheter, the catheter includes a relatively short guide wire lumen 86 for passing the guide wire 82 internal to the occlusion cuff 34, rather than external to the cuff (FIG. 5). The guide wire lumen 86 is preferably on the opposite side of the primary lumen 88 of the catheter, through which the bundle 24 passes, from the secondary, inflation lumen 89. The guide wire lumen has a proximal opening in the side of the catheter wall proximal of the occlusion cuff 34, and a distal opening out the front of the catheter so that a guide wire 82 extends from the guide wire lumen parallel to the bundle 24. The length of the guide wire lumen may be on the order of twice the longitudinal length of the occlusion cuff.

While the catheter combination may take several configurations, some exemplary dimensions will be given for purposes of discussion. In a combination where the reference length of the angioscope is 54 mm, the minimum extension of the angioscope tip beyond the distal catheter tip is 0.036 mm, and the maximum extension is 0.043 mm. The outside diameter of the catheter tip is preferably 0.066 mm while the maximum length of the minor axis (horizontal diameter) of the catheter tip is preferably 0.063 mm. The maximum length (vertical diameter) of the major axis of the angioscope tip is 0.068 mm. The width and height dimensions are within plus or minus 0.003 mm. The maximum length of the angioscope tip from the front face to the extreme rear tip is approximately 0.15 mm, while the maximum vertical rise from the top of the insert sleeve 86 to the top edge of the angioscope tip is approximately 0.009 mm. The maximum diameter of the angioscope bundle is preferably 0.035 mm, while the outside diameter of the insert sleeve is approximately 0.019 mm. The maximum overall length of the insert is preferably 0.12 mm. The length of each scallop cut 88 is preferably approximately 0.02 mm, the start of the front scallop cut beginning approximately 0.02 mm from the front of the insert sleeve. The start of the second or rear scallop cut begins approximately 0.06 mm from the front of the insert sleeve. In the angioscope application, the catheter tube is preferably a 4.5 F catheter. The inside diameter of the primary lumen is sufficient to allow irrigation and injection of fluids, for example saline, radiopaque dyes or medication, within the primary lumen and around the fiber optic bundle. The outer polyvinyl chloride tubing for the bundle encloses the cylindrically arranged polymethyl methacrylate light fibers 68 used for transmitting light from an OPTX 300 light source, capable of converting 300 watts of electrical power into more than 100,000 LUX (lumens per square meter). The light fibers 68 are set in epoxy potting adhesive around the lens and optic fiber bundle. The lens is preferably designed to have a magnification of 1/10 at 5 millimeters.

The optic bundle consists of a fused silica fiber surrounded by preferably eleven acrylic fibers. The fused fiber carries a coherent image from the tip of the bundle to its proximal end. The lens is used to focus images from the artery on the surface of the fiber. The fibers are held together in a PVC jacket measuring 0.6 millimeters in diameter for the last 12 inches of the bundle, and a 0.65 millimeter diameter stainless steel tube for the balance of the bundle.

The catheter consists of a double-lumen polyethylene catheter with a Kraton balloon bonded at the tip. This construction allows superior flexibility which is required to reach small, difficult to access vessels. The catheter also allows infusion of solutions through the primary catheter lumen and around the angioscope bundle.

To introduce and use the catheter combination 20 in a vessel or body cavity, for example, the guide wire 82 is inserted into the target cavity or blood vessel, such as the brachial or ilial artery as is known to those skilled in the art. For angiography, using an angioscope 26, the guide wire is introduced upward into a desired vessel of the cardiac artery until it reaches the desired location. The proximal end of the guide wire external to the patient's body is then threaded through the orifice 84 of the angioscope tip 80, where the tip 26 is extending slightly beyond the catheter tip 30, and the guide wire lumen 86 of the pre-assembled catheter combination. The catheter tip 30 extends distally and the angioscope also extends distally into the desired vessel 90 so that the characteristics of the vessel can be observed. When the catheter and angioscope are in place, and the occlusion cuff inflated if necessary, the physician can begin the procedure to diagnose and/or treat the vascular condition under consideration. Having the guide wire internal to the inflated occlusion cuff allows proper and complete inflation of the cuff against the vessel wall, so that there is no significant leakage around the cuff to interfere with clear viewing of the object of interest through the angioscope. If the guide wire is external to the inflated occlusion cuff, complete occlusion of flow in the vessel may not be achieved in the subject vessel, such as a human coronary vessel.

Once the catheter has been positioned as desired, the angioscope can be maneuvered as desired in order to move the lens closer to the object of interest, or to bring the object of interest into proper focus. This is especially significant where the occlusion cuff has been inflated to fix the catheter in place, but the ability to manipulate the angioscope is still desirable. When the characteristics of the vascular condition, such as a stenotic lesion 92, is determined, the occlusion cuff can be collapsed and the catheter combination removed, while leaving the guide wire 82 in place. Other instruments can then be inserted into the vessel 90 following the guide wire 82 to treat or otherwise operate in the vessel 90. The configuration and construction of the angioscope tip and bundle allow improved access to distal coronary vessels relative to previous angioscopic instruments. Additionally, the optic bundle and catheter are independently moveable inside each other allowing the bundle to be probed down the vessel beyond the catheter without moving the catheter, while still retaining stable guide wire position.

Although the present invention has been described in detail with reference only to the present preferred embodiments, it will be appreciated by those of ordinary skill in the art that various modifications can be made without departing from the spirit of the invention. Accordingly, the invention is limited only by the following claims.

What is claimed is:

1. A method of positioning a catheter assembly including a catheter and an endoscope in a body vessel or cavity for treatment therein, the catheter having a hollow tubular member defining a lumen, the catheter further having a proximal end, a distal end, an inflatable occlusion cuff on the distal end, and a guide wire lumen provided internally of the occlusion cuff, the endoscope having a distal portion with a guide wire tip provided at the endoscope distal portion and with the guide wire tip having an aperture provided therethrough, comprising the steps of:
    insetting a guide wire having a distal tip and a proximal end with the body vessel or cavity until the guide wire distal tip reaches a desired location in the body vessel or cavity;
    extending the endoscope through the lumen of the catheter with the guide wire tip extendable beyond the catheter distal end;
    threading the proximal end of the guide wire through the guide wire tip aperture of the endoscope; and
    threading the proximal end of the guide wire through the guide wire lumen of the catheter.

2. The method of claim 1, further comprising the step of:
    extending the distal portion of the endoscope beyond the distal end of the catheter; and
    moving the endoscope along the body vessel or cavity while the catheter remains at a fixed location within the body vessel or cavity.

3. The method of claim 2, further comprising the steps of: providing the distal end of the catheter with a radiopaque marker; and viewing the location of the distal end of the catheter.

4. The method of claim 2, further comprising the steps of: providing the guide wire tip of the endoscope with a radiopaque marker; and viewing the location of the guide wire tip of the endoscope.

5. A catheter assembly for passing an endoscope along a body vessel or cavity, the assembly comprising:
    a catheter having a hollow tubular member defining a lumen, the catheter having a proximal end, a distal end, an inflatable occlusion cuff on the distal end, and a guide wire lumen provided internally of the occlusion cuff;
    an endoscope having a distal portion with a guide wire tip provided at the endoscope distal portion, the guide wire tip having an aperture provided therethrough, the endoscope extending through the lumen of the catheter with the guide wire tip extendable beyond the catheter distal end; and
    a guide wire external to at least a portion of the catheter hollow tubular member and passing through the guide wire lumen of the catheter and the aperture of the endoscope guide wire tip.

6. The assembly of claim 5 wherein the endoscope distal portion is adapted to extend distally beyond the catheter distal end to move along the body vessel or cavity while the catheter remains in a fixed position in the body vessel or cavity.

7. The assembly of claim 6 wherein the guide wire tip has an elliptically-shaped transverse cross-section.

8. The assembly of claim 6, further comprising a radiopaque marker on the distal end of the catheter.

9. The assembly of claim 6, further comprising a radiopaque marker on the guide wire tip of the endoscope.

10. The assembly of claim 9, further comprising means for inflating the occlusion cuff.

11. The assembly of claim 10, further comprising means for infusing a solution through the catheter lumen.

12. The assembly of claim 11, wherein the infusing means includes an irrigation duct.

13. The assembly of claim 12, wherein the inflating means includes a secondary lumen connected to the occlusion cuff.

14. The assembly of claim 13, wherein the endoscope comprises an angioscope having a distal end and a proximal end, the angioscope comprising a fiber bundle connected to a light connector and an image connector at the angioscope proximal end, and a lens connected to the fiber bundle at the angioscope distal end.

15. The assembly of claim 14, wherein the fiber bundle is encased by a sheath.

* * * * *